(12) United States Patent
Sanders et al.

(10) Patent No.: US 10,640,745 B2
(45) Date of Patent: May 5, 2020

(54) METHOD FOR DEFORMING AND/OR FRAGMENTING A CELL, SPORE OR VIRUS WITH A VIBRATING PLATE

(71) Applicant: TTP PLC, Melbourn, Royston Hertfordshire (GB)

(72) Inventors: Giles Hugo William Sanders, Melbourn (GB); Abi Clair Graham, Melbourn (GB); Rita Stella, Melbourn (GB)

(73) Assignee: TTP PLC, Royston Hertfordshire (GB)

( * ) Notice: Subject to any disclaimer, the term of this patent is extended or adjusted under 35 U.S.C. 154(b) by 880 days.

(21) Appl. No.: 14/891,314

(22) PCT Filed: May 16, 2014

(86) PCT No.: PCT/GB2014/051510
§ 371 (c)(1),
(2) Date: Nov. 13, 2015

(87) PCT Pub. No.: WO2014/184577
PCT Pub. Date: Nov. 20, 2014

(65) Prior Publication Data
US 2016/0083687 A1 Mar. 24, 2016

(30) Foreign Application Priority Data
May 16, 2013 (GB) .................................. 1308946.1

(51) Int. Cl.
| | | |
|---|---|---|
| *C12N 1/06* | (2006.01) | |
| *C12M 1/00* | (2006.01) | |
| *C12M 1/42* | (2006.01) | |
| *C12N 13/00* | (2006.01) | |
| *C12N 5/00* | (2006.01) | |
| *C12N 7/00* | (2006.01) | |

(52) U.S. Cl.
CPC ............. *C12N 1/066* (2013.01); *C12M 35/04* (2013.01); *C12M 47/06* (2013.01); *C12N 5/00* (2013.01); *C12N 7/00* (2013.01); *C12N 13/00* (2013.01)

(58) Field of Classification Search
None
See application file for complete search history.

(56) References Cited

U.S. PATENT DOCUMENTS

2003/0066915 A1    4/2003   Taylor

FOREIGN PATENT DOCUMENTS

| JP | 2009-000023 A | 1/2009 | |
|---|---|---|---|
| WO | WO-2006096303 A2 * | 9/2006 | ......... B05B 17/0646 |
| WO | WO 2013/030761 A1 | 3/2013 | |
| WO | WO 2013/059343 A1 | 4/2013 | |

OTHER PUBLICATIONS

Okpodu, et al. "Rapid isolation of nuclei from carrot suspension culture cells using a BioNebulizer". BioTechniques 16(1):154-159]. (Year: 1994).*
Dehand, R. "Nebulizers that use a vibrating mesh or plate with multiple apertures to generate Aerosol". Respiratory Care. Dec. 2002 . vol. 47, No. 12. pp. 1406-1418. (Year: 2002).*
Goldberg. S. "Mechanical/Physical Methods of Cell Disruption and Tissue Homogenization". From Methods in Molecular Biology vol. 424: 2D Page: Sample Preparation and Fractionation: vol. 1, Anton Posch, Ed. pp. 3-22. (Year: 2008).*
International Search Report from parent PCT Application No. PCT/GB2014/051510, 4 pages (dated Aug. 18, 2014).

* cited by examiner

*Primary Examiner* — Amy L Clark
(74) *Attorney, Agent, or Firm* — Klarquist Sparkman, LLP (57) ABSTRACT

The present invention relates to a method for the deformation and/or fragmentation of a cell, spore or virus, the method comprising: (i) bringing a liquid sample containing the cell, spore or virus into contact with a first surface of a vibratable plate having at least one aperture, and causing the plate to vibrate; and (ii) passing the sample of the cell, spore or virus through the at least one aperture in the vibrating plate so as to cause deformation and/or fragmentation of the cell, spore or virus. It also concerns a device for carrying out the method.

14 Claims, 6 Drawing Sheets

METHOD FOR DEFORMING AND/OR FRAGMENTING A CELL, SPORE OR VIRUS WITH A VIBRATING PLATE

CROSS REFERENCE TO RELATED APPLICATIONS

This is the U.S. National Stage of International Application No. PCT/GB2014/051510, filed May 16, 2014, which was published in English under PCT Article 21(2), which in turn claims the benefit of United Kingdom Application No. 1308946.1, filed May 16, 2013.

The present invention relates to a method and device. In particular, though not exclusively, it concerns a method for the deformation or fragmentation of biological entities such as cells, spores or viruses, and a device for carrying out such a method.

Fragmentation of biological entities, for example cell lysis, can currently be achieved by a number of chemical or mechanical means. Chemical means are conventionally associated with the introduction of enzymes or other chemical reagents to a dispersion of cells to be lysed, and thereby lead to the disruption of the cell structure by chemical degradation. It is also known for chemical strategies to be employed in connection with mechanical methods.

For example, U.S. Pat. No. 6,664,049 discloses a method and device for cell lysis in which a liquid mixture of bacteria or eukaryotic cells and a lysing agent is caused to flow in a steady stream inside a portion of tubing. The flow-rate of this stream is adjusted as a function of the diameter and length of the tubing, and facilitates the attainment of a substantially homogeneous cell lysate at an outlet of the tubing. The lysing agent is typically an alkaline or hypotonic solution.

U.S. Pat. No. 5,837,529 discloses a method for lysing cells which comprises simultaneously flowing a cell suspension and a lysis solution (i.e. a solution containing, a lysing agent) through a static mixer.

U.S. Pat. No. 6,942,169 discloses a method and device for performing lysis on a cell-containing fluid, in which the fluid flows through a vibrating micromachined tube to physically rupture the cell membranes, and/or to mix, agitate or homogenise the fluid during chemical lysis.

However, chemical methods for cell lysis are limited. The use of enzymes is often costly and the overall process is slow, taking extended periods of time for the enzymes to lyse the cells. In addition, the use of chemical reagents introduces otherwise unwanted chemical species into the cell mixture which may potentially interfere with other downstream applications of the lysate obtained.

Mechanical methods are commonly used to physically lyse cells, and include mechanical disruption, liquid homogenisation, sonication (i.e. high-frequency sound waves), freeze/thaw cycles, and manual grinding.

While mechanical disruption methods, e.g. the Waring blender and the Polytron, typically rely on the use of rotating blades to grind and disperse biological matter, liquid homogenisation (one of the most commonly used techniques for small volumes and cultured cells) functions by forcing the biological matter through a narrow space, and thereby shearing the cell membranes. Examples of such devices include the Dounce homogeniser, the French Press, and the Potter-Elvehjem homogeniser.

For example, U.S. Pat. No. 7,176,018 discloses a micromachined cell lysis, device which comprises electrodes that are positioned less than 10 µm from each other. The cells are attracted to the space between the electrodes and then lysed on passage through the limited space.

U.S. patent application Ser. No. 12/718,396 discloses a system for algal cell lysis. The system includes a plurality of metal nanoparticles and an electromagnetic radiation generator. The generator is able to produce radiation which excites the metal nanoparticles, and thereby results in lysis of the algal cells.

The freeze/thaw method is commonly used to lyse bacterial and mammalian cells, and usually involves freezing a cell suspension in a dry ice/ethanol bath or freezer and then thawing the material at room temperature or 37° C. This causes the cells to swell and ultimately break with formation of ice crystals due to the freezing process, and then contract during thawing.

However, such mechanical methods are generally quite expensive and often require multiple passes of the cells through the device. This means that any matter which has been released at an early stage may be subsequently damaged by the additional passes.

In addition, any heat generated by the mechanical action of the device potentially leads to denaturation of the cell contents.

It is also possible to use mechanical microfluidic approaches to mechanically deform cells, such that their membranes become more porous (Sharer et al. PNAS Early Edition, 2013, 1218705110). This can be used to enhance delivery of macromolecules into cells (e.g. for transfection).

It is an object of the present invention, therefore, to provide a method for the deformation or fragmentation of biological entities such as cells, spores or viruses, which overcomes the disadvantages stated above.

It is also an object of the invention to provide a device for carrying out the above method.

According to the invention, there is provided a method for the deformation and/or fragmentation of a cell, spore or virus, the method comprising:
  (i) bringing a liquid sample containing the cell, spore or virus into contact with a first surface of a vibratable plate having at least one aperture, and causing the plate to vibrate; and
  (ii) passing the sample of the cell, spore or virus through the at least one aperture in the vibrating plate so as to cause deformation and/or fragmentation of the cell, spore or virus.

As used herein, the term 'fragmentation' refers to the break-up or rupture of the cell, spore or virus structure such that its contents are at least partially released. Thus, the term encompasses any extent of rupture, provided that biological contents are liberated in order to allow further processing or analysis thereof. More preferably, fragmentation refers to the process of lysis. The term 'deformation' refers to a change in the physical integrity of the cell etc., such that the outer membrane (and/or wall where present) becomes more permeable or porous to external molecular species, such as macromolecular species (e.g. polynucleotides), present outside the cell etc. (e.g. for the purpose of transfection). Deformation may also include the formation of temporary pores in the membrane and/or cell walls such that material from the cell may be shared with an external fluid. This can entail the transport of material from external media to the cell (e.g. as in the case of transfection) and/or the transport of material from the cell to external media for downstream analysis. Deformation may be caused by relaxation of the cell etc. following compression of the cell etc. on passage through the at least one aperture in the vibrating plate. Such deformation does not include lysis, and at least a proportion of the cells remain viable.

Deformation or fragmentation of the cell, spore or virus structure is efficiently achieved by the passage of the sample through the at least one aperture in the plate upon vibration of the plate. The shear forces, mechanical impact, and/or ultrasonic effects (e.g. ultrasonic cavitation) exerted by the vibration of the plate are sufficient to break the biological structure, whilst being mild enough to avoid any unwanted degradation of the contents released. In addition, it has been found that the method usually only requires one pass of the sample through the at least one aperture in the plate to cause effective rupture, although further passes are possible as a means to improve overall efficiency. The method of the present invention is efficient, involves a minimal number of steps, does not cause damage to the contents of the cell etc. once liberated, and does not have any adverse effects on downstream applications of the products obtained.

In order to achieve cell etc. deformation as opposed to fragmentation using the process, it is possible to vary such parameters as aperture diameter, vibration frequency, plate velocity etc. In particular, where the average (e.g. mean) aperture diameter is chosen such that it is, for example, 20 to 170% (e.g. 20 to 120%, 30 to 110%, 40 to 105%, preferably 50 to 120%, 55 to 110%, 60 to 100%, most preferably 50 to 100%) of the average cell diameter in the sample, deformation will be the predominant process. Thus, deformation (e.g. for the purposes of transfection) may dominate when the average aperture diameter is similar to the average cell etc. diameter in the sample. Conversely, where the average aperture diameter is, for example, less than 70% (e.g. less than 60%, less than 50%, preferably less than 45%, less than 40%, or less than 35%) of the average cell diameter in the sample, fragmentation (e.g. lysis) may dominate.

The method may further comprise (iii) collecting the deformed and/or fragmented products, i.e, the cells etc. (or fragments thereof) following their passage through the vibratable plate. In this case, the method is particularly suited to applications in which the sample is employed in downstream processing and/or analysis. For example, if fragmentation or deformation of the sample releases DNA, the product may be further subjected to PCR (polymerase chain reaction) in order to amplify for analysis the contents of the sample.

It will be understood that, in embodiments where deformation of the cell etc. is desired, the liquid sample may also contain one or more exogenous macromolecules for intracellular delivery (e.g. polynucleotides, in the case of the use of the method for transfection).

The term 'transfection' as used herein refers to a process of intentionally introducing one or more nucleic acid species (e.g. DNA or RNA) into cells etc. (e.g. eukaryotic cells), for example for the purposes of causing the cells etc. to express a polypeptide encoded by the nucleic acid.

In a particularly preferred embodiment, the plate is a mesh having a plurality of apertures.

The method of the invention may be initiated upon vibration of the plate. This vibration may be characterised by any vibrational mode that causes the plate to displace or deform to generate pressure waves. In particular, deformation of the plate causes the plate to be displaced, at least partially, in a direction perpendicular to the plane of the plate. In some embodiments, deformation of the plate causes the at least one aperture in the plate to enlarge and contract. Preferably, the vibration of the plate has an amplitude of 0.1 to 100 μm, or 1 to 30 μm, more preferably 0.1 to 5 μm or 2 to 10 μm. Furthermore, the vibration of the plate may have a frequency of 5 to 200 kHz, 20 to 150 kHz, 35 to 120 kHz, or 50 to 100 kHz, preferably 70 to 100 kHz.

The means by which the plate is caused to vibrate is not particularly limited. Any method which creates oscillations in the plate (and thus pressure waves in the medium adjacent the plate) may be suitable for the cells, spores or viruses to become deformed and/or fragmented on passage through the at least one aperture. In a preferable embodiment, the method functions effectively when the vibration of the plate is caused by means of an actuator, such as a piezoelectric actuator. The actuator may be directly bonded to the plate or may be physically connected but separable from the plate by means of a mechanical or other connection (such as a vacuum). The actuator may be activated by supply of an electric potential difference, preferably an alternating potential difference (preferably in kHz ranges).

The types of biological entities which may be subjected to the present method include prokaryotic cells, such as bacteria and archaea, and various forms of eukaryotic including animal cells, protozoa, fungi, algae, plant cells and microscopic plants (green algae). In addition, spores (usually haploid and unicellular) and viruses may also be processed. The biological entities may comprise either single cells (unicellular), cell clusters or may be made up of multicellular complex structures (e.g. tissues, organs or partially digested forms thereof). In a preferable embodiment, the cell, spore or virus is selected from mammalian cells, bacterial cells, fungal cells, plant cells, algal cells, spores and viruses. For practical reasons, mammalian cells, bacterial cells, and fungal cells are especially preferred. In particular for human and animal diagnostics, mammalian cells selected from blood cells (e.g. erythrocytes), circulating tumour cells and mucous membrane cells (e.g. cheek cells) are preferred.

In some embodiments of the invention, it may be even more advantageous to include other additional means to aid fragmentation. For example, glass, polymeric or metal-containing beads or particles of a size larger than the apertures in the plate, and typically but not exclusively spherical or spheroidal in shape, may be added to the sample containing the cell, spore or virus. Alternatively or additionally, reagents to accelerate cell lysis such as enzymes, detergents and/or salts may be added to the sample containing the cell, spore or virus.

Where the vibration of the plate is produced by application of an electric potential difference to an actuator in operational connection with the plate, the vibration of the plate may be driven by a particular waveform. The drive waveform may therefore be represented by a wave or oscillation obtained from the change in electrical signal as a function of time. For example, the vibration of the plate may have a drive waveform which is sinusoidal, square, sawtooth or triangular. Preferably, the drive waveform is sinusoidal, square, or triangular. In a potentially favourable embodiment, the drive waveform of the vibrating plate is pulsed with a duty cycle (the percentage on-time in a continuously processed sample) of between 0.01 to 100% (preferably 0.01 to 1%) and duty period of 100 ms to 20 s (preferably 1 ms to 2 s).

One advantage of the invention resides in the fact a range of volumes of samples, from small (<10 μl) to large (>10 ml), may be efficiently processed. Thus, the average flow-rate of the sample through the device is not particularly limited, but is usually dependent on the nature of the sample being treated. Preferably, the passage of the sample through the vibrating plate has an average flow-rate of 1 pl/min to 200 ml/min, more preferably 100 nl/min to 10 ml/min or 1 nl/min to 25 ml/min.

As mentioned above, the method of the invention is sufficiently effective that only one pass of the sample through the device may be required for deformation or fragmentation to occur to a desired level. It is possible, however, to include further passes of the sample through the device, if required, for further improved results. This may be achieved in a couple of ways. First, the method may be carried out for one or more additional times by repeating steps (i)-(iii) by means of recycling the collected products back to the first surface of the vibrating plate, i.e. in a cyclic process. Alternatively, the method may be carried out for one or more additional times by repeating steps (i)-(iii) by means of bringing the collected products into contact with a first surface of at least one further vibrating plate arranged downstream, i.e. additional devices arranged in series with one another.

In a further embodiment, the method of the invention may further comprise at least one known method of cell lysis carried out before, during or after the steps defined above, such as a known method selected from mechanical lysis, liquid homogenisation, sonication, freeze-thaw cycling, manual grinding, and chemical lysis (as described above).

In a further embodiment, the method of the invention may further comprise at least one known method of transfection carried out before, during or after the steps defined above, such as a known method selected from chemical-based transfection, non-chemical-based transfection, and/or particle-based transfection. For example, electroporation, sonoporation, optical transfection, protoplast fusion, impalefection, hydrodynamic delivery, gene gun therapy, magnetofection, particle bombardment, viral transduction, and/or nucleofection.

Chemical-based transfection can be divided into several kinds: for example, using calcium phosphate precipitation, cyclodextrin, polymers, liposomes, or nanoparticles.

One of the simplest methods uses calcium phosphate. HEPES-buffered saline solution (HeBS) containing phosphate ions is combined with a calcium chloride solution containing the DNA to be transfected. When the two are combined, a fine precipitate of the positively charged calcium and the negatively charged phosphate forms, binding the nucleic acid species to be transfected on its surface. The suspension of the precipitate is then added to the cells to be transfected. The cells take up some of the precipitate, and with it, the nucleic acid species.

Other methods use highly branched organic compounds, such as dendrimers, to bind the DNA and get it into the cell. Another method is the inclusion of the nucleic acid species to be transfected in liposomes, which can fuse with the cell membrane, releasing the nucleic acid species into the cell. Transfection may sometimes be increased using cationic liposomes (or mixtures). Another method involves the use of cationic polymers such as DEAE-dextran or polyethylenimine. The negatively charged peptide species binds to the polycation and the complex is taken up by the cell via endocytosis.

With regard to non-chemical methods, electroporation (gene electrotransfer) is a popular method, where transient increase in the permeability of cell membrane is achieved when the cells are exposed to short pulses of an intense electric field. Cell squeezing is a more modern method which enables delivery of molecules into cells by a gentle squeezing of the cell membrane. It is a high throughput vector-free microfluidic platform for intracellular delivery.

Sonoporation uses high-intensity ultrasound to induce pore formation in cell membranes. This pore formation is attributed mainly to the cavitation of gas bubbles interacting with nearby cell membranes. Optical transfection is a method whereby a small (~1 μm diameter) hole is transiently generated in the plasma membrane of a cell using a highly focused laser.

Protoplast fusion is a technique in which transformed bacterial cells are treated with lysozyme in order to remove the cell wall. Following this, fusogenic agents (e.g. Sendai virus, PEG, or electroporation) are used in order to fuse the protoplast carrying the gene of interest with the target recipient cell. A major disadvantage of this method is that bacterial components are non-specifically introduced into the target cell as well.

Impalefection is a method of introducing nucleic acid species bound to a surface of a nanofiber that is inserted into a cell. This approach can also be implemented with arrays of nanofibers that are introduced into large numbers of cells and intact tissue.

In relation to particle-based methods, one direct approach to transfection is the gene gun, where the nucleic acid species is coupled to a nanoparticle of an inert solid (commonly gold) which is then "shot" directly into the target cell's nucleus.

Magnetofection, or magnet assisted transfection, which uses magnetic force to deliver DNA into target cells. Nucleic acids are first associated with magnetic nanoparticles. Then, application of magnetic force drives the nucleic acid particle complexes towards and into the target cells, where the cargo is released.

Another particle-based method of transfection is particle bombardment. The nucleic acid species is delivered through membrane penetration at a high velocity, usually connected to microprojectiles.

In viral methods, adenoviral vectors can be useful because they can transfer genes into a wide variety of human cells.

Based on the physical method of electroporation, nucleofection uses a combination of electrical parameters with cell-type specific reagents. The substrate is transferred directly into the cell nucleus and the cytoplasm.

According to another aspect of the invention, there is provided a device for the deformation and/or fragmentation of a cell, spore or virus, the device comprising:
  a plate comprising at least one aperture extending from a first surface of the plate to a second surface of the plate;
  an actuator in operational connection with the plate so as to cause the plate to vibrate upon activation of the actuator; and
  a reservoir containing a liquid sample of the cell, spore or virus in fluid connection with the first surface of the plate.

The type of actuator is not particularly limited, as long as actuation creates oscillations in the plate, and hence pressure oscillations in the liquid sample containing the cell, spore or virus which facilitates its passage toward the first surface of the plate and through the at least one aperture therein. For example, actuation may be initiated by supply of an electric potential difference, preferably an alternating potential difference. In a particularly effective embodiment, the cell, spore or virus becomes deformed and/or fragmented on passage through the at least one aperture when actuation is achieved using a piezoelectric actuator.

It will be understood that, in embodiments where deformation of the cell etc. is desired, the liquid sample may also contain one or more exogenous macromolecules for intracellular delivery. In a further embodiment, the one or more exogenous molecular (such as macromolecular) species may be presented adjacent to the second surface of the plate, i.e. such that the cells etc. encounter such species following passage through the plate. Such an embodiment may also be applied to the method of the present invention.

In a particularly preferred embodiment, the plate is a mesh having a plurality of apertures extending from a first surface of the mesh to a second surface of the mesh.

The device may further comprise a receptacle into which the sample of the deformed and/or fragmented cell, spore or virus can be delivered upon passage through the at least one aperture in the plate. The presence of such a receptacle then facilitates the processing of the deformed or fragmented products in downsteam analytical applications, such as those including sample clean-up, PCR, proteomic analysis, the measurement of concentration of one or more analytes in the resulting samples, which may be genomic, proteins, lipids and small molecules, ions and other intracellular or cell wall constituents. In these embodiments, the receptacle may contain one or more exogenous macromolecules for intracellular delivery to cells etc. deformed by passage through the at least one aperture.

The utility of the device may also be further enhanced when the device further comprises a resilient member, such as an additional plate (with or without one or more apertures, preferably non-vibratable), positioned in registration with the second surface of the vibratable plate. The positioning of a resilient member at a suitable distance from the vibratable plate can enhance the fragmentation of the cell etc. passing through the at least one aperture in the plate.

In order to improve operational control of the device, it may further comprise a valve in fluid connection with the second surface of the plate. Such a valve may be in biased connection with the second surface of the plate and may thus be operated in a range of different positions between fully open and closed. The valve is therefore one means which may be employed to control the flow-rate of the sample through the plate, in addition to the actuator.

The plate for use in the process or device of the invention is preferably composed of a material which is resilient enough to ensure longevity of use, yet has a certain level of flexibility that allows it to be transiently displaced and/or flex upon actuation of the device. Suitable materials include metal, ceramic, glass, or polymer. Preferably, the plate is composed of metal.

The at least one aperture in the plate is not particularly limited in terms of its shape and may be circular or non-circular. In a preferable aspect, the at least one aperture has a substantially non-circular shape. For example, the at least one aperture may be substantially square, triangular, oval, or slot-shaped in cross-section.

In terms of size, the at least one aperture in the mesh preferably has at least one diameter which is in the range of 10 nm to 100 µm more preferably 25 nm to 60 µm, even more preferably 50 nm to 40 µm. For the fragmentation of mammalian cells, such as red blood cells, an aperture size in the range of 50 nm to 40 µm, more preferably 200 nm to 20 µm, is most effective in terms of yield and selectivity.

The device according to the invention is in fluid connection with a sample containing a cell, spore or virus. For example, the sample may contain mammalian cells, bacterial cells, fungal cells, plant cells, algal cells, spores and/or viruses. Preferably, the sample contains at least one type of mammalian cell, bacterial cell, fungal cell or virus. In an advantageous embodiment, the conditions of the method and device may be tailored such that one type of cell, spore or virus is selectively fragmented in favour of another cell, spore or virus that may also be present in the sample. In particular, mammalian cells, e.g. cancer cells may be selectively fragmented (preferably lysed) in preference over other cells in the sample, or red blood cells may be selectively fragmented (preferably lysed) in preference over other cells (e.g. other blood cells) in the sample, leaving the remaining cells viable for further manipulation. This may be achieved by modifying a number of factors, including but not exclusively limited to the choice of aperture size, vibrational amplitude of the plate, duty cycle of the vibration, and positioning of apertures on the plate with respect to the vibration. The device is also effective in the fragmentation of fungal cells, e.g. yeasts, for which large amplitudes of vibration are typically employed.

For example, in the method of the invention, the parameters of plate size, aperture size, positioning of the at least one aperture in the plate, vibration frequency and/or velocity of plate movement may be selected such that one type of cell, spore or virus is preferentially deformed and/or fragmented compared to another type of cell, spore or virus. In this embodiment, it will be appreciated that the person skilled in the art would readily be able to determine, through routine trial and error, suitable conditions using the parameters mentioned herein whereby certain cells etc. may be selectively deformed and/or fragmented over other types of cell etc.

In another aspect of the invention, there is provided a container comprising, a device according to the invention, and a receptacle, wherein the device is detachably mounted on a surface of the receptacle, such that a liquid sample passed through the device passes into or out of the receptacle.

In particular, the device may be detachably mounted on a wall, a floor, on or in a lid, or at a mouth of the receptacle. In addition, the container may be a bottle, cuvette, well plate, or vial. The configuration of the device in such a location allows for simultaneous deformation and/or fragmentation and dispensing of the sample. The configuration also allows for simple replacement of the device if a different sample is to be subjected to cell etc. deformation and/or fragmentation, thereby avoiding the possibility of cross-contamination. It may also be easily replaced if in need of repair. The device may be disposable for similar reasons.

According to a further aspect of the invention, there is provided a use of a device according to the invention, for the deformation and/or fragmentation of a cell, spore or virus. Such a use is preferably for the deformation (for example, for the purposes of intracellular delivery of macromolecules (e.g. polynucleotides), such as for transfection) and/or lysis of mammalian cells, bacterial cells, fungal cells, plant cells, algal cells, spores or viruses (more preferably mammalian cells, bacterial cells, or fungal cells).

In embodiments of the invention, the method, device, container or use is for deformation of the cells etc. In further embodiments, the method, device container or use is for fragmentation of the cells etc.

The invention will now be described in more detail by way of example only, and with reference to the following figures.

BRIEF DESCRIPTION OF THE FIGURES

FIG. 1

Analytical, results of mammalian blood lysates at concentration levels of 2 µl of 250 µl/ml, 125 µl/ml and 15 µl/ml used to provide a DNA template for qRT-PCR. The cycle threshold (Ct) values are averages of two duplicates, and relate to the number of cycles required for the fluorescent signal to cross the threshold (i.e. exceed the background level). The Ct values are inversely proportional to the amount of target nucleic acid in the sample, i.e. the lower the Ct value the greater the amount of nucleic acid in the sample. The results marked 9/10 and 10/10 indicate lysate duplicates were prepared independently.

Key:
+=cells lysed and DNA purified using a QIAamp DNA Mini Kit (QIAGEN) prior to qRT-PCR.
−=cells unlysed.
The final bar with no fill represents the result of a no-template control.

FIG. 2

Analytical results of PCR reaction products obtained after a single pass of a sample containing mammalian blood cells through a vibratable membrane having an average aperture diameter of 4.6 μm.

Key:
+=PCR reaction including purified gDNA.
−=No template for reaction.
Unlys.=250 μl whole blood diluted in water to a final volume of 1 ml (1/4 dilution), and 2 μl added to PCR reaction.
Others=indicated volumes of whole blood diluted in water to a final volume of 1 ml, lysed using the device of the invention, and 2 μl of lysates added to 50 μl PCR reactions.

FIG. 3

Analytical results of the amplification of DNA from mammalian blood lysates using alternative DNA polymerases.

Key:
+=PCR reaction including purified gDNA.
−=No template for reaction.
In all cases, the indicated volumes of whole blood were diluted in water to a final volume of 1 ml, lysed using the device of the invention (or unlysed), and 2 μl of lysates added to 50 μl PCR reactions.

FIG. 4

Analytical results using greater volumes of blood in PCR reactions. The results show that PCR can be carried out even when large volumes of blood lysate are added to the reaction mix.

Key:
+=PCR reaction including purified gDNA.
−=No template for reaction.
Unlys.=250 μl whole blood diluted in wales to a final volume of 1 ml (1/4 dilution), and 2 μl added to PCR reaction.
Others=250 μl whole blood diluted in water to a final volume of 1 ml (1/4 dilution), lysed using the device of the invention, and the indicated volumes added to 50 μl PCR reactions.

FIG. 5

Analytical results of PCR using (i) DNA in blood lysate or (ii) DNA purified from blood lysate using a Nexttec sorbent column. The Nexttec sorbent filter was used to purify DNA from blood lysed using the device of the invention, with no inhibitory effects on subsequent PCR.

Key:
+=PCR reaction including purified gDNA.
−=No template for reaction.
Purification of DNA using Nexttec cleanColumns was then used for PCR, with 2 μl added to PCR reaction.

FIG. 6

Analytical results of DNA purified from PCR reactions performed on blood lysate, using Nexttec sorbent columns. The Nexttec sorbent filter effectively purifies PCR-amplifted DNA (prepared using lysate taken from the device of the invention as a source of template for PCR).

Key:
+=PCR reaction including purified gDNA.
−=No template for reaction.

FIG. 7

Microscopy of samples containing mammalian blood cells before (top) and after (bottom) being subjected to a single pass through the device according to the invention.

FIG. 8

Microscopy of samples containing yeast cells before (top) and after (bottom) being subjected to a single pass through the device according to the invention.

FIG. 9

Microscopy of samples containing, mammalian blood cells and bacterial cells before (top) and after (bottom) being subjected to a single pass through the device according to the invention. The images show that blood cells may be selectively lysed in favour of the bacterial cells. The inserts show fluorescent scans (Using a TTP Labtech Acument Explorer system) of the sample treated with a calcein (live/dead) dye, indicating that the bacterial cells survived the treatment and the blood cells were selectively lysed

FIG. 10

The data shown is a fluorescent readout of a sample (200 μL) of a mammalian, Jurkat, cell line that has been incubated with FITC labelled antibody and then washed. The antibody cannot permeate the plasma membrane of viable cells. A1 and A2 show a sample that has not passed through the device. A3 and A4 show the output of cells that have been passed through a device with 13 μm apertures and into a solution of the FITC labelled antibody before washing. The considerable difference in the fluorescence measurement suggests the device provides considerable poration of the cells and transfer of the antibody through the membrane.

FIG. 11

A schematic view of a device according to the invention. 1 is a liquid sample containing a cell, spore or virus. 2 is an actuator, such as a piezo ring. 3 is an area of plate containing at least one aperture. 4 is a system holder. 5 is a plate.

FIG. 12

A fluorescent image of a sample of a mammalian, Jurkat, cell line (containing approximately 50,000 cells/mL) passed through a device according to the invention in the presence of an Alexa Fluor-labelled IgG antibody. The image was measured using a TTP Labtech Mirrorball system (TTP Labtech, Melbourn, UK).

FIG. 13

The data shown compares the intracellular delivery (in nominal units of fluorescence) of Alexa Flour-labelled IgG labelled antibody into a sample of a mammalian, Jurkat, cell line containing approximately 50,000 cells/mL and having a cell size of approximately 20 μm) following passage through the device according to the invention. Subsequent labelling was performed with calcein-AM and a Hoechst counter stain. The Hoechst counter stain labels all cells and the calcein is only converted in live cells to give a fluorescent entity, thereby providing a measurement of the live:dead ratio (i.e. viability) of the cells in the treated sample.

EXAMPLES

Figure 11:
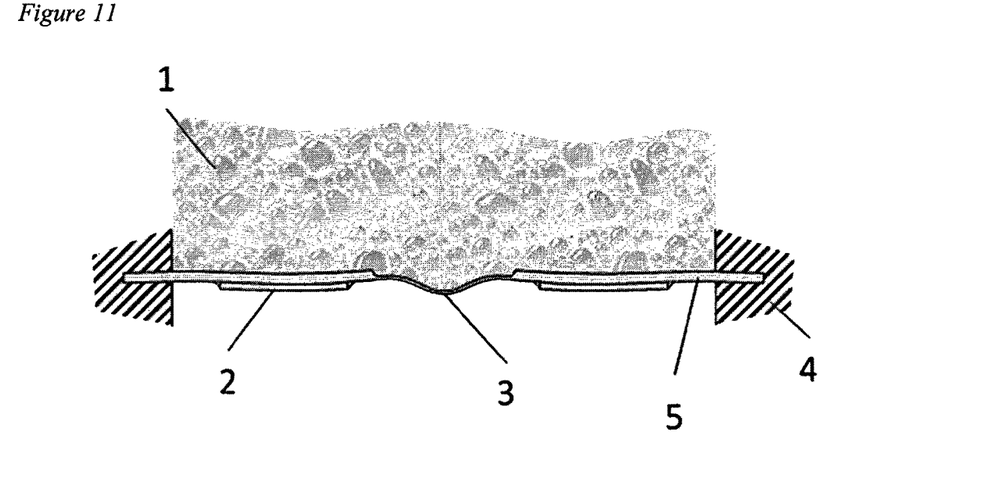

A device according to the invention (see FIG. 11) was employed in the following examples.

Example 1

Quantification of DNA Purified from Blood Lysates

TABLE 1

| Blood sample | DNA in lysates (µg/ml) | Theoretical maximum DNA in lysates (µg/ml) |
|---|---|---|
| 250 µl/ml (¼) | 0.5-3 | 11.3 |
| 125 µl/ml (⅛) | 0.2-1.2 | 5.6 |
| 15 µl/ml (1/66) | 0.05-0.2 | 0.7 |
| 250 µl/ml (¼, unlysed) | 0.01-0.04 | — |

Table 1 above shows concentrations of DNA purified from lysates, as calculated using Picogreen reagent, Invitrogen. DNA purification procedure: QIAamp Mini Kit, QIAGEN. Results obtained using vibratable mesh having 4.6 µm pore diameter, and flow rate of ~150 µl lysate per minute. Theoretical maximum yields of DNA were calculated by assuming, that there are 7000 white blood cells per µl of blood, and that each cell contains 6.8 pg DNA. Therefore, quantification of DNA purified from blood lysates indicated that large quantities of DNA are released by the device of the invention.

Example 2

Levels of DATA in Lysates

Figure 1:
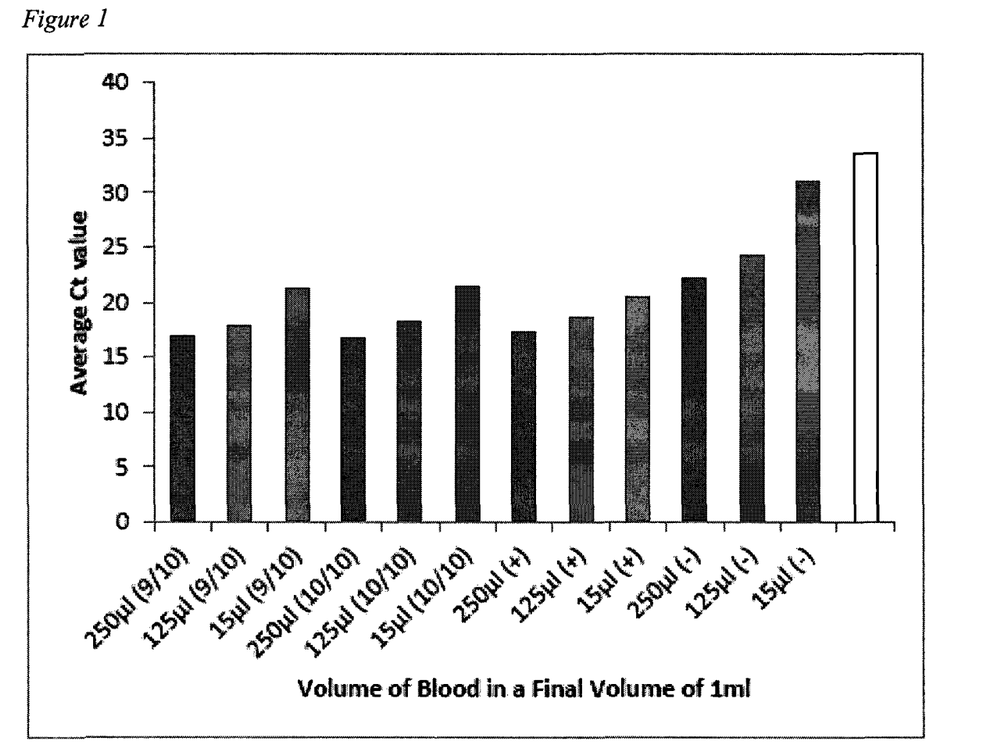

FIG. 1 shows concentration levels of 2 µl of 250 µl/ml, and 15 µl/ml of the lysates which were used to provide a DNA template for qRT-PCR. The Ct values are averages of two duplicates. The results marked 9/10 and 10/10 indicate lysate duplicates were prepared independently.
+ =cells lysed and DNA purified using QIAamp DNA Mini Kit (QIAGEN) prior to qRT-PCR.
− =cells unlysed.
The final bar with no till represents the result of a no-template control.
Therefore, qRT-PCR suggests that levels of DNA in lysates produced by the device are least comparable to those produced by commercially-available kits.

Example 3

DNA Released from Cells During Lysis of Diluted Blood

Figure 2:
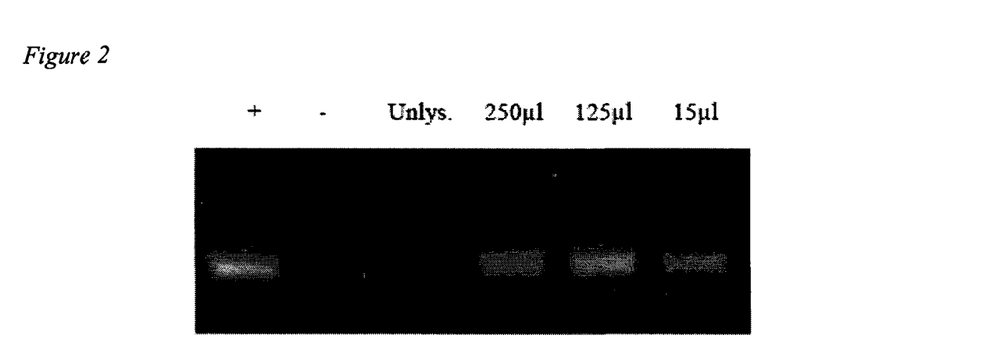

FIG. 2 shows that a single pass through the vibratable mesh (4.6 µm pore diameter) releases more than enough DNA to be used as a template for PCR. No subsequent purification of DNA was required before PCR.
The PCR reaction products (HatStarTaq, QIAGEN) were analysed on 2% agarose gel.
+ =PCR reaction including purified gDNA.
− =No template for reaction.
Unlys.=250 µl whole blood diluted in water to a final volume of 1 ml (1/4 dilution), and 2 µl added to PCR reaction.
Others=indicated volumes of whole blood diluted in water to a final volume of 1 ml, lysed using the device if the invention, and 2 µl of lysates added to 50 µl PCR reactions.

Therefore, DNA released from cells during lysis of diluted blood can be used as a template for PCR without prior purification of the DNA.

Example 4

Amplification DATA from Blood Lysates

Figure 3:
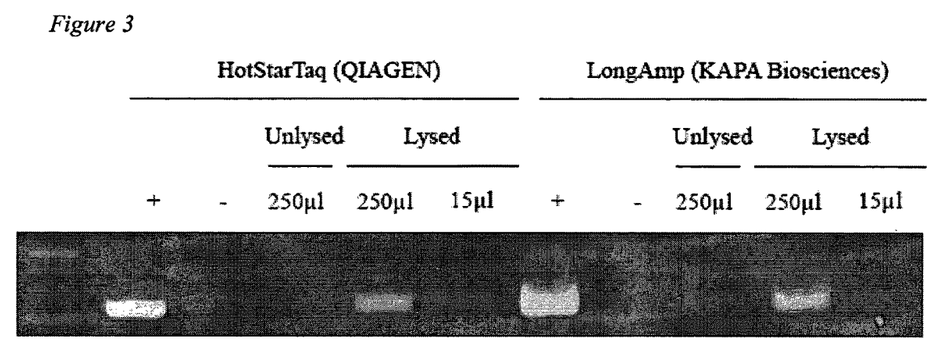

FIG. 3 shows that the ability to PCR directly from blood lysate produced by the device of the invention is not limited to one DNA polymerase. The PCR reaction products were analysed on 2% agarose gel.
+ =PCR reaction including purified gDNA.
− =No template for reaction.
In all cases, the indicated volumes of whole blood were diluted in water to a final volume of 1 ml, lysed using the device of the invention (or unlysed), and 2 µl of lysates added to 50 µl PCR reactions.
Therefore, many DNA polymerases can be used to amplify DNA from blood lysate produced by the device of the invention.

Example 5

Assessment of Greater Volumes of Blood in PCR Reactions

Figure 4:
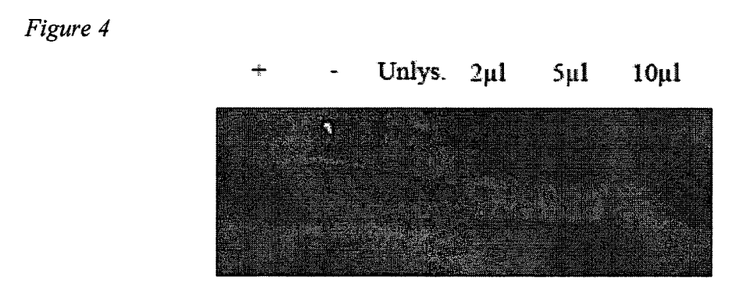

FIG. 4 shows that greater volumes of blood in PCR reactions do not significantly inhibit the process, PCR is still possible even when large volumes of blood lysate are added to the reaction mix, PCR reaction products (HotStarTaq, QIAGEN) analysed on 2% agarose gel.
+ =PCR reaction including purified gDNA.
− =No template for reaction.
Unlys.=250 µl whole blood diluted in water to a final volume of 1 ml (1/4 dilution), and 2 µl added to PCR reaction.
Others=250 µl whole blood diluted in water to a final volume of 1 ml (1/4 dilution), lysed using the device of the invention, and the indicated volumes added to 50 µl PCR reactions.
Therefore, using greater volumes of blood in PCR reactions does not significantly inhibit the process.

Example 6

Figure 5:
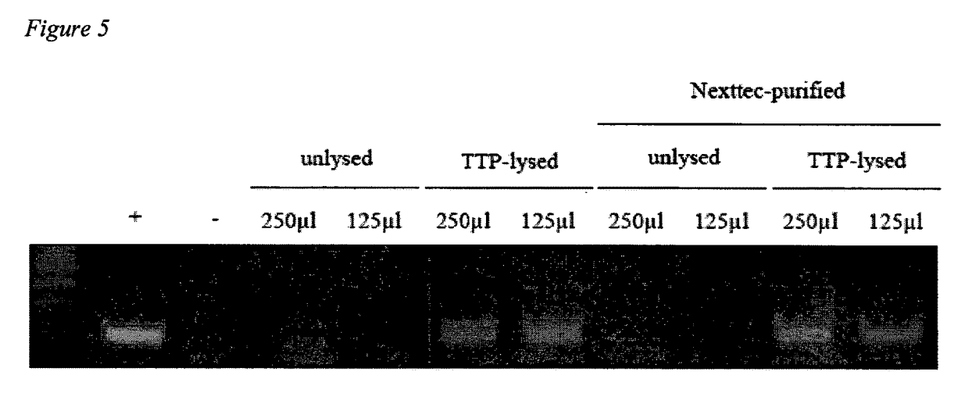

FIG. 5 shows that PCR is possible using (i) DNA in blood lysate or (ii) DNA purified from blood lysate using a Nexttec sorbent column. A Nexttec sorbent filter was used to purify DNA from blood lysed using the device of the invention, with no inhibitory effects on subsequent PCR. The PCR reaction products (HotStarTaq, QIAGEN) were analysed on 2% agarose gel.
+ =PCR reaction including purified gDNA.
− =No template for reaction.
Purification of DNA using Nexttec cleanColumns were then used for PCR, with 2 µl added to PCR reaction.
Therefore, PCR is possible using (i) DNA in blood lysate or (ii) DNA purified from blood lysate using a Nexttec sorbent column.

Example 7

Figure 6:
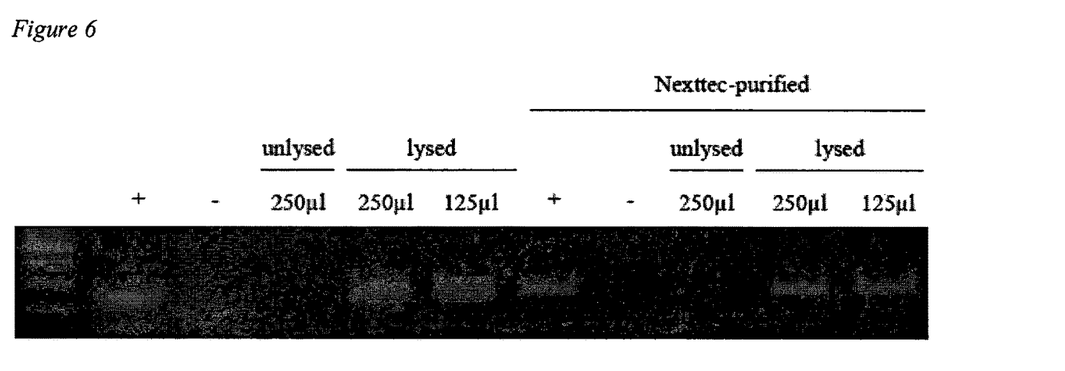

FIG. 6 shows that DNA can be efficiently purified from PCR reactions performed on blood lysate, using Nexttec sorbent columns. The Nexttec sorbent filter can effectively purify PCR-amplified DNA (prepared using lysate obtained from the device of the invention as a source of template for PCR). The PCR reaction products (HotStarTaq, QIAGEN) were analysed on 2% agarose gel. DNA purified from PCR reactions using Nexttec cleanColumns as indicated.

Therefore, DNA can be efficiently purified from PCR reactions performed on blood lysate, using Nexttec sorbent columns.

Example 8

Figure 7:
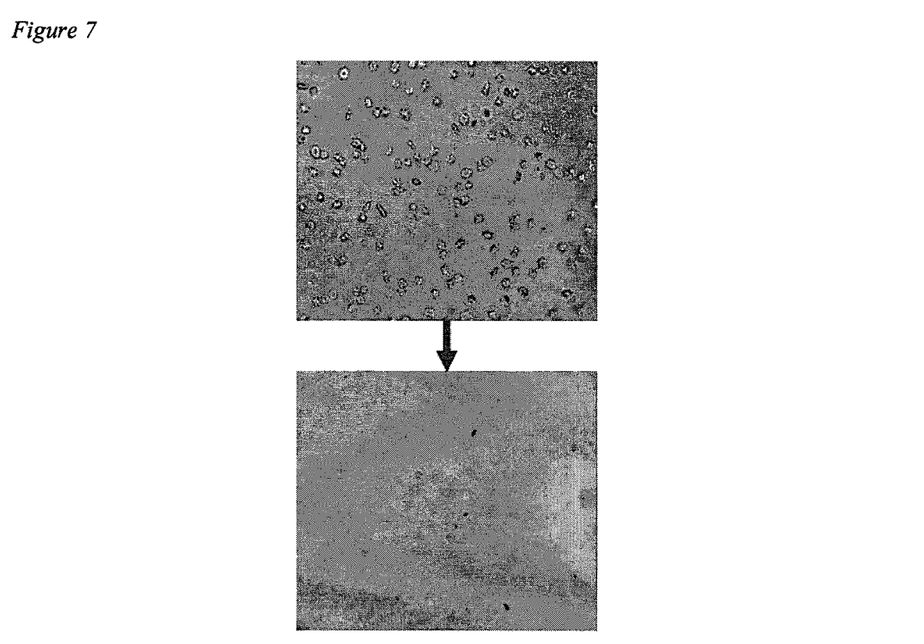

Light microscopy was carried out on porcine blood before and after transition through the device of the invention. In this case, the system employed 3 micron apertures and the cells were effectively lysed. The resulting image is shown in FIG. 7.

Example 9

Figure 8:
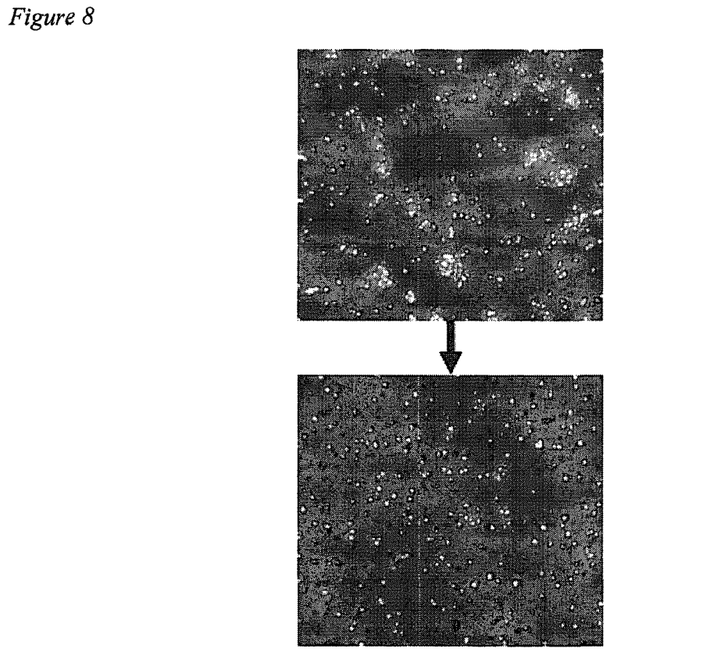

Dark field microscopy was carried out on yeast cells before and after transition through the device of the invention. A considerable increase in the damaged and empty cells was seen. In this case, the system employed 3 micron apertures. The resulting image is shown in FIG. 8.

Example 10

Figure 9:
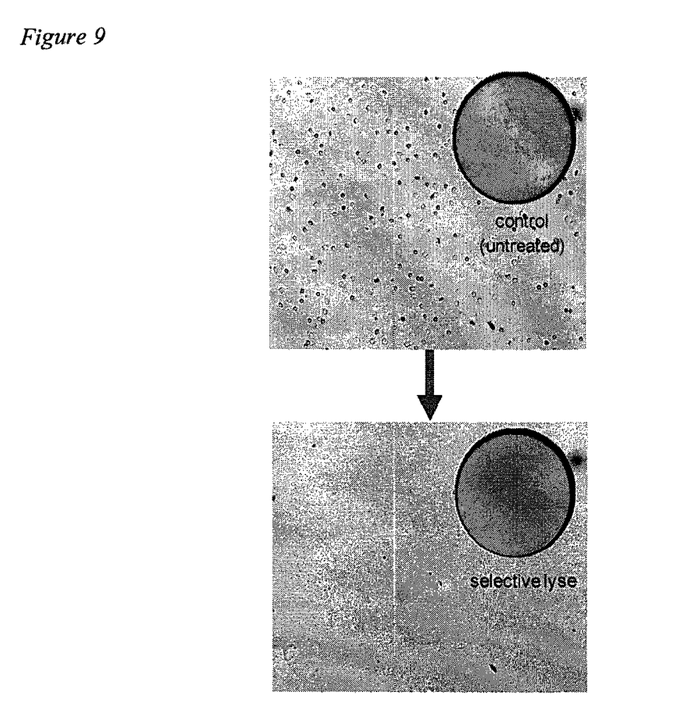

Light microscopy was carried out on a porcine blood/bacteria mix (Serratia marcescens) before and after passage through a 4 micron aperture device according to the invention. The resulting image is shown in FIG. 9.

Example 11

Figure 10:
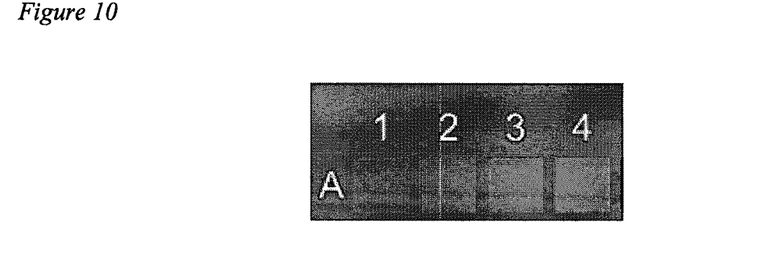

Enhanced macromolecular delivery to cells by use of the method and device of the invention. A sample (200 µl) of a mammalian cell line was incubated with FITC labelled antibody and then washed. The antibody could not permeate the plasma membrane of viable cells. Fluorescence data was obtained with samples that had not been passed through the device and with cells that had been passed through a device with 13 µm apertures and into a solution of the FITC labelled antibody before washing (see FIG. 10). The considerable difference in the fluorescence measurement suggests the device provides considerable poration of the cells and transfer of the antibody through the membrane.

Example 12

Mammalian Jurkat cells were prepared and diluted to approximately 50,000 cells/mL. The cell suspension was mixed with an Alexa Fluor-labelled antibody. The suspension was then passed through a device according to the invention (at ca. 80 kHz) in which the sizes of the apertures of the vibrating plate are detailed below. The material having passed through the device according to the invention was imaged on a TTP Labtech Mirrorball system and the extent of cell permeability analysed by cell fluorescence. The samples were then incubated with calcein-AM and a Hoechst counter stain, whereby the Hoechst counter stain labels all cells and the calcein is only converted in live cells to give a fluorescent entity. This enabled measurement of the live:dead ratio (i.e. viability) of the cells in the samples.

Figure 12:
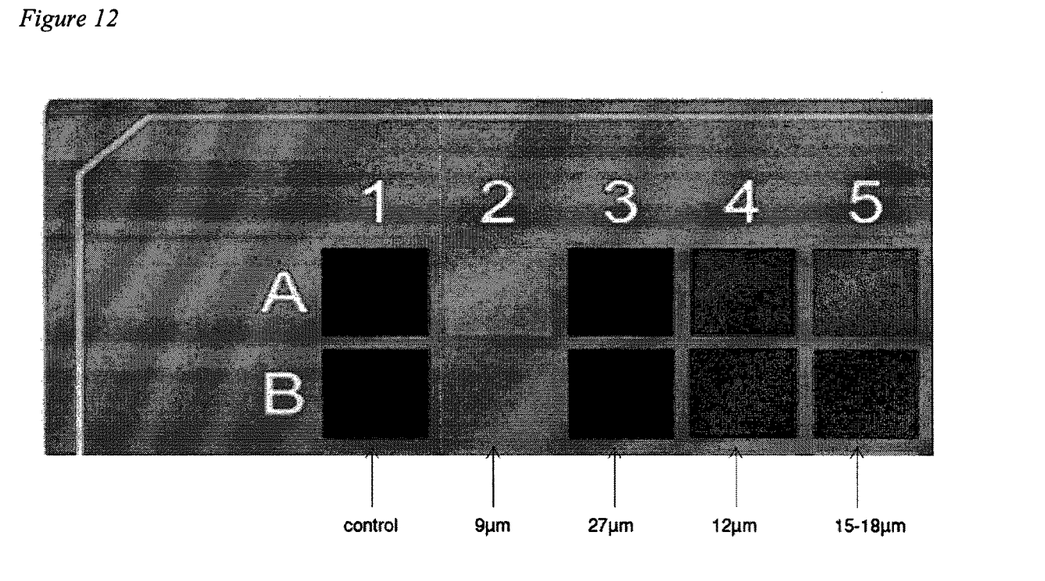

In FIG. 12, A1 and B1 show a sample that has not passed through the device according to the invention, i.e. a negative control. A2 and B2 show cells that have been passed through a device according to the invention with 9 µm apertures with a solution of the Alexa Fluor-labelled antibody. A3 and B3 show cells that have been passed through a device according to the invention with 27 µm apertures. A4 and B4 show cells that have been passed through a device according to the invention with 12 µm apertures. A5 and B5 show cells that have been passed through a device according to the invention with 15-18 µm apertures. The enhanced fluorescence measurements for A2/B2, A4/B4 and A5/B5 suggest the device according to the invention provides considerable poration (enhanced permeability) of the cells and transfer of the antibody through the membrane, yet results in cells which remain viable.

Figure 13:
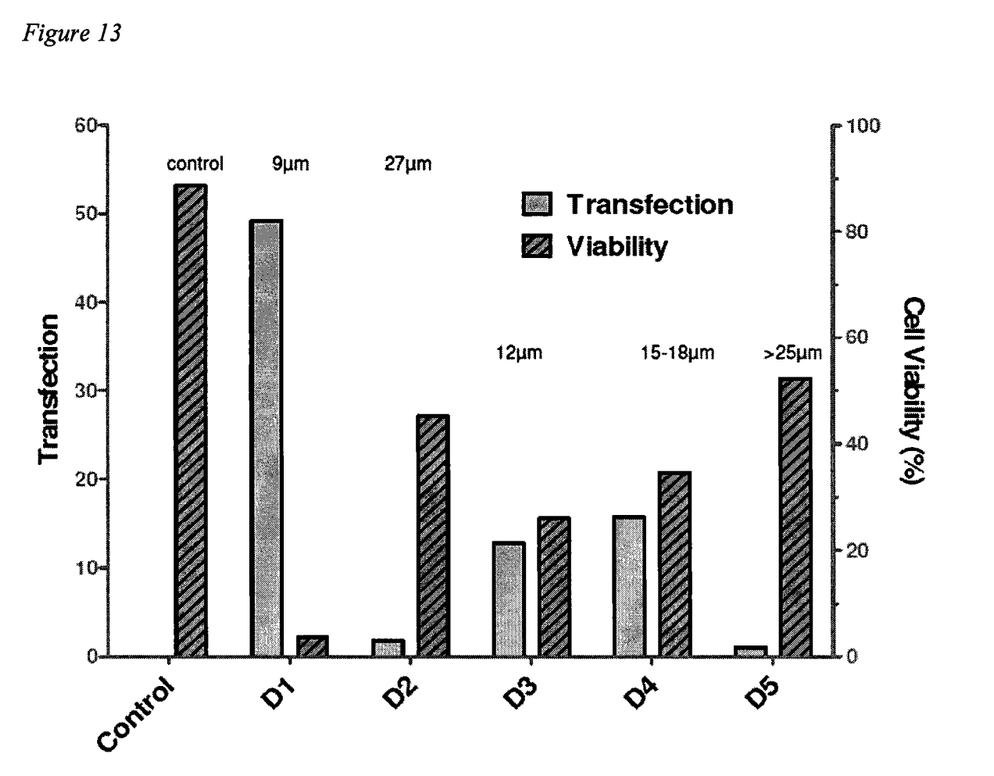

In FIG. 13, D1 shows a sample that has been passed through a device according to the invention with 9 µm apertures, resulting in a high level of deformation and a low level of cell viability (i.e. a high level of cell lysis). D2 shows a sample that has been passed through a device according to the invention with 27 µm apertures, resulting in a low level of deformation and approximately 50% cell viability. D3 and D4 show samples that have been passed through a device according to the invention with 12 µm apertures and 15-18 µm apertures, respectively, resulting in a good level of deformation and a good level of cell viability. D5 shows a sample that has been passed through a device according to the invention with >25 µm apertures, resulting in a low level of deformation and a high level of cell viability. These results therefore collectively show that cells passing through apertures of a similar size to the size of the cells are deformed (e.g. so as to facilitate enhanced intracellular macromolecular delivery) to a significant level and that the cells remain viable. Thus, when the macromolecular species is a nucleic acid species, transfection can be enhanced due to the improved delivery of the nucleic acid species into the cell. In addition, the results show that apertures of a smaller size than the size of the cells tend more to result in fragmentation (and potentially lysis) of the cells.

Given that a relatively high vibrational amplitude was employed in this experiment, it may be expected that lower vibrational amplitudes could lead to improved survival rates of the cells (i.e. enhanced viability) with similar levels of deformation.

The invention claimed is:

1. A method for deforming and/or fragmenting a cell, a virus, or a mixture thereof, wherein the cell is a bacterial cell, yeast cell, mammalian cell, or blood cell, the method comprising:
    (i) bringing a liquid sample containing the cell, virus, or mixture thereof into contact with a first surface of a vibratable plate having at least one aperture, and causing the plate to vibrate;
    (ii) passing the liquid sample containing the cell and/or virus through the at least one aperture in the vibrating plate to cause a) deformation of the cell and/or virus by shear force, mechanical impact and/or ultrasonic effects, and/or b) fragmentation of the cell and/or virus; and
    (iii) collecting a liquid comprising the deformed or fragmented cell and/or virus.

2. The method according to claim 1, wherein the at least one aperture has an average diameter of 20 to 170% relative to the diameter of an average cell or virus in the liquid sample.

3. The method according to claim 1, wherein relaxation of the cell and/or virus after passing of the cell and/or virus through the at least one aperture causes the outer membrane and/or wall of the cell and/or virus to become more permeable to external molecular species.

4. The method according to claim 1, wherein the method is for fragmenting the cell and/or virus and wherein the at least one aperture has an average diameter of less than 70% relative to the average diameter of the cell or virus.

5. The method according claim 1, wherein the vibratable plate is a vibratable mesh having a plurality of apertures.

6. The method according to claim 1, wherein vibration of the plate causes the plate to be displaced perpendicular to the plane of the plate.

7. The method according to claim 1, wherein vibration of the plate is caused by a piezoelectric actuator.

8. The method according to claim 1, comprising deforming or fragmenting the cell.

9. The method according to claim 1, wherein beads are added to the liquid sample containing the cell, virus, or mixture thereof.

10. The method according to claim 1, wherein enzymes and/or salts are added to the liquid sample containing the cell, virus, or mixture thereof.

11. The method according to claim 1, wherein the vibration of the plate has an amplitude of 0.1 to 5 μm and a frequency of 5 to 200 kHz.

12. The method according to claim 1, wherein plate size, aperture size, positioning of the at least one aperture in the plate, vibration frequency and/or velocity of plate movement are selected to deform and/or fragment the cell or virus as compared to a different cell or virus, respectively.

13. The method according to claim 1, further comprising chemical-based transfection, non-chemical-based transfection, and/or particle-based transfection.

14. The method according to claim 1, wherein relaxation of the cell and/or virus following passing of the cell and/or virus through the at least one aperture causes the outer membrane and/or wall of the cell and/or virus to become permeable to external macromolecular species.

* * * * *